US006609015B2

(12) United States Patent
Lucassen et al.

(10) Patent No.: US 6,609,015 B2
(45) Date of Patent: Aug. 19, 2003

(54) ANALYSIS OF A COMPOSITION

(75) Inventors: Gerhardus Wilhelmus Lucassen, Eindhoven (NL); Gerwin Jan Puppels, Rotterdam (NL); Peter Jacobus Caspers, Rotterdam (NL); Marjolein Van Der Voort, Eindhoven (NL); Egbert Lenderink, Eindhoven (NL); Martinus Bernardus Van Der Mark, Eindhoven (NL); Robert Frans Maria Hendriks, Eindhoven (NL); Julius Simon Cohen, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/912,127

(22) Filed: Jul. 24, 2001

(65) Prior Publication Data
US 2002/0133065 A1 Sep. 19, 2002

Related U.S. Application Data
(60) Provisional application No. 60/262,582, filed on Jan. 18, 2001.

(51) Int. Cl.[7] .................................................. A61B 5/00
(52) U.S. Cl. ........................ 600/322; 600/407; 600/316; 600/476
(58) Field of Search ................................. 600/322, 316, 600/407, 476; 128/664, 665, 633

(56) References Cited

U.S. PATENT DOCUMENTS

| | | | | |
|---|---|---|---|---|
| 4,541,438 A | * | 9/1985 | Parker et al. ................ | 128/664 |
| 5,303,026 A | * | 4/1994 | Strobl et al. ................. | 356/318 |
| 5,370,114 A | * | 12/1994 | Wong et al. ................. | 600/322 |
| 5,657,754 A | * | 8/1997 | Rosencwaig ................. | 600/316 |
| 5,795,295 A | * | 8/1998 | Hellmuth et al. ........... | 600/407 |
| 5,814,820 A | | 9/1998 | Dong et al. ............... | 250/458.1 |
| 5,865,738 A | * | 2/1999 | Morcos et al. .............. | 600/365 |
| 5,865,754 A | * | 2/1999 | Sevick-Muraca et al. ... | 600/476 |
| 5,941,821 A | * | 8/1999 | Chou .......................... | 600/316 |
| 6,002,958 A | * | 12/1999 | Godik .......................... | 600/407 |
| 6,029,079 A | * | 2/2000 | Cox et al. .................. | 144/134.1 |
| 6,210,346 B1 | * | 4/2001 | Hall et al. ................... | 600/561 |

FOREIGN PATENT DOCUMENTS

EP          0339582 A2      9/1998      .......... G01N/21/64

* cited by examiner

Primary Examiner—Hieu T. Vo
Assistant Examiner—Johnny H. Hoang
(74) Attorney, Agent, or Firm—John Vodopia

(57) ABSTRACT

An analysis apparatus including a spectroscopic analysis apparatus comprises an excitation system and a monitoring system. The excitation system emits an excitation beam to excite a target region during an excitation period. The monitoring system emits a monitoring beam to image the target region during a monitoring period. The excitation period and the monitoring period substantially overlap. Hence the target region is imaged together with the excitation, and an image is formed displaying both the target region and the excitation area. On the basis of this image, the excitation beam can be very accurately aimed at the target region.

20 Claims, 10 Drawing Sheets

ANALYSIS OF A COMPOSITION

CROSS REFERENCE TO RELATED APPLICATIONS

This application claims the benefit of U.S. Provisional Application Ser. No. 60/262,582 filed Jan. 18, 2001, the teachings of which are incorporated herein by reference.

BACKGROUND OF THE INVENTION

1. Field of the Invention

In general, analysis apparatus, such as spectroscopic analysis apparatus are used to investigate the composition of an object to be examined. In particular, analysis apparatus employ an analysis, such as a spectroscopic decomposition, based on interaction of the matter of the object with incident electromagnetic radiation, such as visible light, infrared or ultraviolet radiation.

2. Description of the Related Art

Conventional analysis apparatus is known from the U.S. Pat. No. 6,069,690, incorporated herein by reference The known analysis apparatus concerns a dual mode integrated laser imaging and spectral analysis system, which is used to view and analyse defects on a work piece such as a semiconductor wafer. This known analysis apparatus has two operating modes, namely a scanned imaging mode and a stop scan spectral analysis mode. During the scanned imaging mode a monitoring beam in the form of a laser beam is emitted and the target region is imaged. Separately from the imaging, in the stop scan mode, the laser beam is employed for excitation and spectral analysis can be carried out.

SUMMARY OF THE INVENTION

An object of the invention is to provide an analysis apparatus which supplies an analysis of a target comprised in the object to be examined more reliably than the known analysis apparatus.

This object is achieved by an analysis apparatus according to the invention wherein the excitation period and the monitoring period substantially overlap.
During the overlap of the excitation period and the monitoring period the excitation of the target region and the monitoring of the target region occur simultaneously and/or alternatingly. Because the target region is imaged together with the excitation, an image is formed displaying both the target region and the excitation area. On the basis of this image the excitation beam can be very accurately aimed at the target region. Consequently, the excitation beam generates scattered radiation almost exclusively in the target region, or at least the target region is included in the area that is excited by the excitation beam. The scattered radiation from the target region is detected and the composition of the target region is derived from the scattered radiation.

In particular the analysis apparatus performs spectral analysis of the scattered radiation from the target region to determine the material composition. For the excitation beam various types of electromagnetic radiation, notably ultraviolet radiation, visible light or infrared radiation can be employed. Owing to the excitation scattered radiation may be generated by different physical mechanisms of interaction of the excitation beam with matter in the excitation area. Scattered radiation includes elastically scattered radiation, inelastically scattered radiation or other types of emission such as fluorescence or phosphorescence, or scattering by multi-photon excitation or non-linear scattering generated by the excitation beam. For example Raman scattering or fluorescence due to single or multi-photon excitation may be generated by the excitation.

In particular, the spectroscopic analysis apparatus according to the invention is advantageously employed to examine in vivo the composition of blood in a capillary vessel of a patient to be examined. In this application the target area is the capillary vessel which is typically located about 50–150 μm under the skin surface. This capillary vessel is imaged by the monitoring system and the excitation beam is accurately directed to the capillary vessel. For example near-infrared radiation is used for excitation of Raman scattering. The Raman scattered radiation is spectroscopically analysed. It appears that the in vivo Raman spectra obtained with the spectroscopic analysis apparatus of the invention have about the same quality, spectral resolution and signal-to-background ratio, as for Raman spectra of human blood obtained in vitro.

Monitoring of the target region can be performed in several ways, preferably the monitoring beam is employed to illuminate the target region with its surroundings and image the target region with its surroundings by way of the reflected monitoring beam from the target region. The reflected monitoring beam may return from the target region and its surroundings either by specular or diffuse reflection and by back-scattering. As an alternative, in the event the object to be examined is to some extent transparent for the monitoring beam, the monitoring beam having been transmitted through the target region may be employed to image the target region. The excitation beam having passed through the target region may be imaged onto the image of the target region in order to display the excited area in the image of the target region.

Preferably, the analysis apparatus according to the invention includes a beam combination unit, which directs the monitoring beam and the excitation beam to the target region. The beam combination further separates the reflected monitoring beam and at least part of the reflected excitation beam from the scattered radiation. Hence, the scattered radiation on the one hand and the reflected monitoring beam with at least part of the reflected excitation beam can be detected separately. From the detected scattered radiation there is information obtained relating to the local composition at the target region. For example the local composition concerns the molecular composition in a small area. The reflected monitoring beam is used to image the target region. The reflected excitation beam can also be imaged in the image of the target region. The image of the target region then shows the actual target and also the location where the excitation is done relative to the target. On the basis of the image it is easy to direct the excitation beam exactly onto the target.

In an example of an analysis apparatus of the invention, the beam combination unit reflects the scattered radiation preferably substantially to a detection system. Several examples of detection systems may be employed depending on the type of scattered radiation. A Raman-spectrometer may be employed for detecting inelastically scattered radiation, notably such as Raman scattered radiation. To detect fluorescently scattered radiation a fluorescence spectrometer is used. The beam combination unit transmits the reflected monitoring beam preferably substantially and transmits the reflected excitation beam from the target region at least partially to an imaging system incorporated in the monitoring system to form the image displaying the target region and the excitation area. In an other example of the analysis apparatus of the invention the beam combination unit reflects the reflected excitation beam from the target region at least partially and the reflected monitoring beam preferably substantially to form the image displaying the target region and the excitation area. In that example the scattered radiation due to the excitation beam is preferably substantially transmitted to the detection system. In the examples of the analysis apparatus of the invention as defined herein the scattered radiation can be separated spatially from the reflected monitoring beam and the reflected excitation beam.

In a further example of the analysis apparatus of the invention, the scattered radiation is separated in time from the reflected monitoring beam and the reflected excitation beam. The same spatial aperture is shared by these beams alternatingly in that in separate time slots, the scattered radiation is passed to the detector system and the reflected monitoring beam is passed to the imaging system, respectively. In a preferred embodiment of the analysis apparatus of the invention alternatingly sharing the spatial aperture through which the various beams, the scattered radiation, the reflected monitoring beam and the reflected excitation beam, is achieved in that the partial transmission alternates partial reflection of these respective beams. In a simple way the alternation of reflection and transmission is achieved by moving a reflector/transmission unit having reflective and transmissive sections that are moved relatively to the various beams. Preferably a rotatable reflector/transmission unit is used which turns the reflective and transmissive sections into and out of the various beams.

Another preferred embodiment of the analysis apparatus of the invention employs yet another variation of sharing the spatial aperture. In this embodiment the reflector/transmission unit of the beam combination unit has a reflective section, preferably a small portion in the centre of the reflector/transmission unit that directs the excitation beam to the excitation area. The reflective section is substantially opaque for the reflected monitoring beam The reflector/transmission unit has a transmissive section, preferably a larger area surrounding the reflective section, which transmits the reflected monitoring beam to the imaging system. The excitation beam is focussed onto the reflective section and reflected and preferably converged into a parallel excitation beam and focussed onto the target region. Part of the (reflected) monitoring beam is intercepted by the reflective section as it is opaque for the (reflected) monitoring beam and the reflective section causes a low-brightness spot in the image formed by the imaging system. For example, the monitoring beam is scanned over the reflector/transmission unit so that also the reflected monitoring beam is scanned over the reflector transmission unit. The image formed by the imaging system will then comprise a low-intensity spot corresponding to the opaque reflective section, which indicates where the excitation beam is directed. The image also shows the target region so that is easy to bring the target area into correspondence with the excited area.

In a variation of the analysis apparatus of the invention the excitation beam and the scattered radiation are substantially transmitted through the transmissive section. This transmissive section is for example formed as a small opening in the reflector/transmission unit, preferably in the centre of the reflector/transmission unit. The reflective section is substantially reflective for the monitoring beam and the reflected monitoring beam. For example the reflective section is formed as the surrounding area around the small opening that acts as the transmissive section. This opening is imaged as a low-brightness spot in the image and marks the excitation area that is reached by the excitation beam.

These reflection and transmission properties are achieved by means of wavelength dependent filters and reflectors. These reflectors and filters are discussed in more detail with reference to the detailed embodiments and with reference to the drawings. Notably, the separation of respective beams is achieved because the scattered radiation, such as Raman scattered radiation or multi-photon fluorescence, has a wavelength that is different from the wavelengths of excitation beam and of the monitoring beam In a further preferred embodiment the monitoring beam and the excitation beam are derived from a single radiation source. Preferably an infrared or optical laser is used to generate the output beam which is then split by a beam splitter, such as a dividing prism or a semi-transparent mirror into the monitoring beam and the excitation beam. This preferred embodiment has a relatively simple and less expensive set-up which only uses a single radiation source.

Preferably, the analysis apparatus comprises a monitoring system including a confocal optical imaging system, such as a confocal video microscope. Good results are particularly obtained with a confocal laser scanning video microscope. The confocal optics focuses the monitoring beam onto a focal plane at the target region and also images this focal plane on the imaging system, notably on to an image pick-up device. The confocal optics of the monitoring system achieves that mainly, or even almost exclusively a region of the object to be examined is imaged where the monitoring beam is focussed. Thus, by changing the focussing of the monitoring beam, the region being imaged can be selected and the image is not or hardly at all disturbed by adjacent portions of the object to be examined. According to the invention also the detection system that receives the scattered radiation is confocally related to the confocal video microscope. The confocal detection accomplishes that the scattered radiation that reaches the detector mainly, or essentially only, originates from the focus of the excitation beam. Preferably, a detection pin-hole is arranged in front of the detector and the scattered radiation is focussed on this detection pin-hole while the excitation beam is focussed on the target region. In particular a fibre entrance can function as the detection pin-hole. Hence, this preferred embodiment of the analysis apparatus according to the invention focuses the monitoring beam and the excitation beam onto the target area and forms an image of the focal plane of the monitoring beam and detects scattered radiation essentially only from the focal plane of the excitation beam. Since the focal planes of the excitation beam and the monitoring beam coincide, scattered radiation is received at the detection system from the target area being monitored in the image formed by the reflected monitoring beam.

Further, the confocal video microscope can adjust the position of the focal plane along the direction normal to the focal plane. Thus, the depth of the target region can be adjusted. During displacement of the focal plane into the depth of the object the confocal relation of the detection system with the confocal optical imaging system achieves that the scattered radiation received by the detector originates from the target region. This preferred embodiment is in particular advantageous to analyse blood in a capillary vessel under the skin surface of a human or animal to be examined.

In a further preferred embodiment of the analysis apparatus according to the invention, the orthogonal polarised spectral imaging arrangement is employed in the monitoring system. In this embodiment a spectrally relatively narrow polarised monitoring beam is employed. The reflected monitoring beam is imaged through an analyser at orthogonal polarisation direction relative to the polarisation direction of the monitoring beam. Hence, substantially only multiply diffused depolarised radiation reaches the imaging system to form a substantially uniform background. Portions in the object to be examined, notably in the target region that substantially absorbs the spectrally narrow monitoring beam are then imaged as low brightness in the image. The monitoring system also images the reflected excitation beam in the same image so that the target region and the excitation area are easily brought into correspondence. Orthogonal polarisation spectral imaging is known per se from the paper 'Orthogonal polarisation spectral imaging: a new method for study of microcirculation' by W. Groner et al. in Nature Medicine 5(1999)1209–1213 to study the morphology of the vessel structure.

Other suitable options for the monitoring systems are for example an optical coherence tomography (OCT) arrangement, an optical Doppler tomography (ODT) arrangement, a photo-acoustic imaging (PAI) arrangement, or a multiphoton microscopy (MPM) arrangement. Notably, the OCT, ODT and PAI arrangements give good results for monitoring blood vessels or other target areas that lie deeper, up to several millimeters, under the skin surface. The MPM arrangement in conjunction with confocal imaging provides a high resolution where details of 3–5 μm are rendered well visible. The MPM arrangement is further suitable for imaging details at a depth up to 0.25 mm.

In a further preferred embodiment an acousto-optic modulator is included in the beam combination unit. In the acousto-optic modulator an acoustic wave is generated which causes diffraction of the various beams. Both a standing as well as a running acoustic wave may be employed. A running acoustic wave is employed in combination with a scanning monitoring beam. In particular the zeroth order diffracted excitation beam and the first order diffracted monitoring beam reach the target region. The first order reflected monitoring beam and the first order diffracted scattered radiation and the first order reflected excitation beams are passed to the imaging system. The zeroth order diffracted scattered radiation is passed to the detection system.

In a further preferred embodiment of the analysis apparatus of the invention the excitation beam is scanned transversely to the longitudinal axis of the target region. This preferred embodiment is especially advantageous for examining elongate target regions of which the longest size is along the longitudinal axis. As the excitation beam scans across the elongate target area, the probability of receiving at least in part scattered radiation from the target region is greatly enhanced.

A further object of the invention is to provide a method of spectral non-invasive analysis of the composition of blood in vivo. It is noted that in spite of numerous attempts to achieve this object made over the last decades, these attempts were unsuccessful in that satisfactory signal-to-background ratio of the spectrum of blood in vivo could not be obtained. Notably as to non-invasive glucose monitoring L. Heinemann et al, in 'Diabetes Technology & Therapeutics, Vol. 2, pp 211–220, 2000) note that "Despite the more than 20 years of intensive research, numerous publications and encouraging announcements, until now no reliable system has been developed" In the paper 'Capillary blood cell velocity in human skin capillaries located perpendicularly to the skin surface: measured by a new laser Doppler anemometer.' by M. Stücker et al. in Microvascular Research 52(1006)188 only success is reported as to measurement of the velocity of blood cells, but not on the composition of the blood. From the U.S. Pat. No. 5,615,673 it is known per se to employ Raman spectroscopy to blood and tissue. However, this known method detects Raman scattered radiation from both capillary vessels at issue as well as to a large extent from tissue between the skin surface and the capillary vessel and hence the detected Raman spectra do not hava a satisfactory signal-to-background ratio of the spectrum of blood in vivo.(In the international application WO92/15008 a method for investigating tissue by means of Raman spectroscopy is disclosed. The U.S. Pat. No. 5,372,135 mentions analysis of blood from differential optical absorption spectra. In the paper 'A Noninvasive Glucose Monitor: Preliminary Results in Rabbits' by Mark S. Borchert, et al in Diabetes Technology & Therapeutics Volume 1, Number 2, 1999, application of Raman spectroscopy to a rabbit's eye is discussed. The U.S. Pat. No. 5,553,616 discloses an analysis by means of an artificial neural network discriminator of Raman scattering intensity to determine glucose concentration in e.g. the skin of an index finger. In that known analysis satisfactory signal-to-background ratio of the spectrum of blood in vivo could not be obtained. Notably this appears to be due to lack of accurate detection of the baseline. Moreover, faithful representation of glucose blood level from measurements at the eye appears to be questionable. Hence, these known methods of analysis do not provide a sufficiently high signal-to-noise ratio. Notably in the overview paper 'Overview of non-invasive glucose measurement using optical techniques to maintain glucose control in diabetes mellitus' by R. W. Waynant et al. in the Leos Newsletter Volume 12 Number 2 April 1998 it is remarked that: 'Current instrumentation lacks specificity due to substantial chemical and physical interferences.'

The present invention satisfies the long-felt need for accurate in vivo analysis of human or animal blood, an is particularly suitable to obtain accurate measurement of the glucose content in human blood in viva. Preferably, the excitation beam is an infrared laser beam and the scattered radiation is Raman scattered infrared radiation.

BRIEF DESCRIPTION OF THE DRAWINGS

These and other aspects of the invention will be elucidated with reference to the embodiments described hereinafter and with reference to the accompanying drawing wherein.

DETAILED DESCRIPTION OF THE PREFERRED EMBODIMENT

Figure 1:
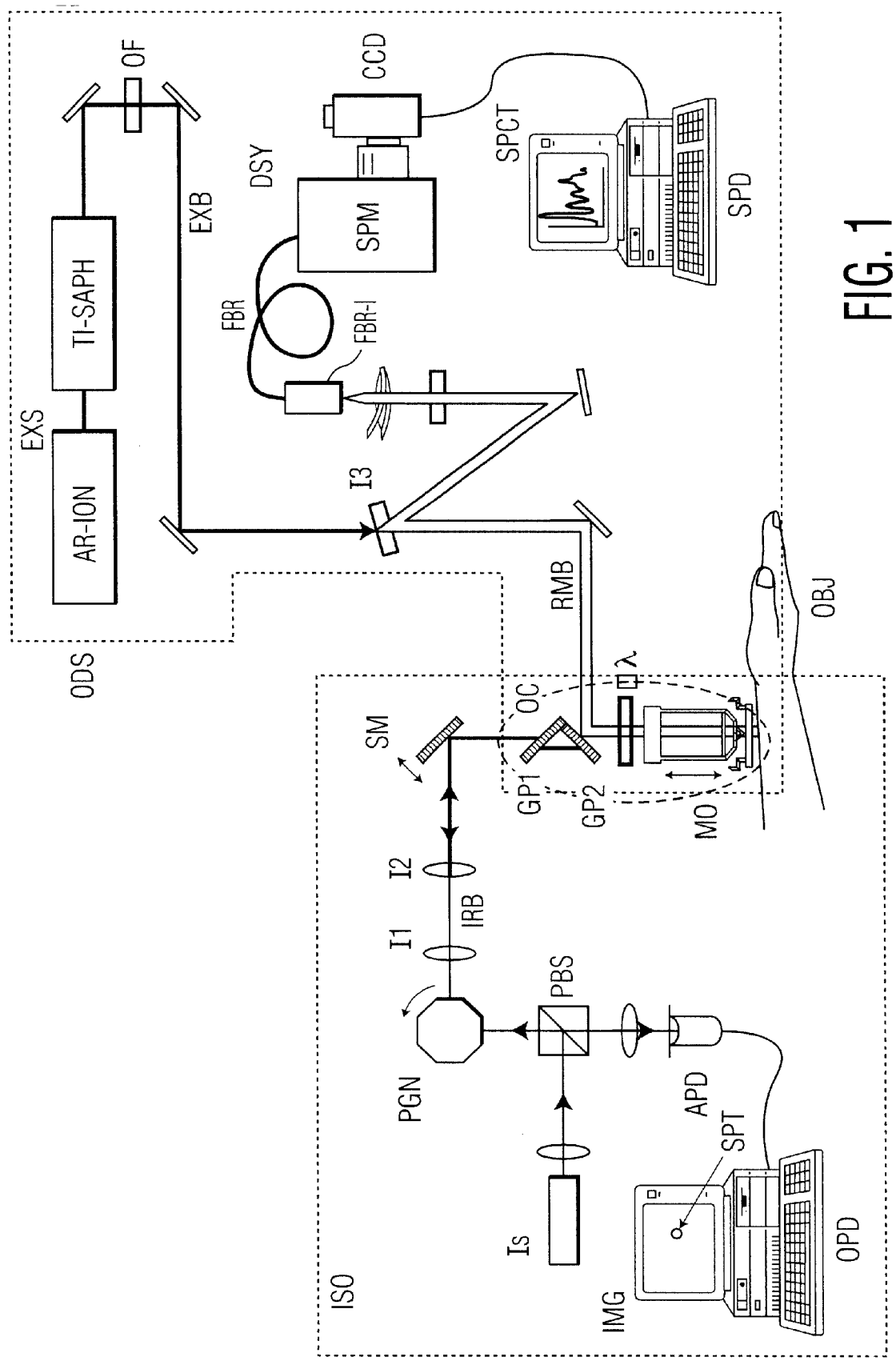
FIG. 1 is a graphic representation of an analysis system in accordance with the invention.

FIG. 1 is a graphic representation of an analysis system in accordance with the invention. The analysis system includes the monitoring system incorporating a light source (ls) with optical imaging system (lso) for forming an optical image of the object (obj) to be examined. The optical imaging system (lso) forms the confocal video microscope. In the present example the object is a piece of skin of the forearm of the patient to be examined. The analysis system also includes a multi-photon, non-linear or elastic or inelastic scattering optical detection system (ods) for spectroscopic analysis of light generated in the object (obj) by a multi-photon or non-linear optical process. The example shown in FIG. 1 utilises in particular an inelastic Raman scattering detection system (dsy) in the form of a Raman spectroscopy device. The term optical encompasses not only visible light, but also ultraviolet radiation and infrared, especially near-infrared radiation.

The light source of the light source with optical imaging system (lso) is formed by an 834 nm AlGaAs semiconductor laser whose output power on the object to be examined, that is, the skin, amounts to 15 mW. The infrared monitoring beam (irb) of the 834 nm semiconductor laser is focussed in the focal plane in or on the object (obj) by the optical imaging system in the exit focus. The optical imaging system includes a polarising beam splitter (pbs), a rotating reflecting polygon (pgn), lenses (11, 12), a scanning mirror (sin) and a microscope objective (mo). The focussed monitoring beam (irb) is moved across the focal plane by rotating the polygon (pgn) and shifting the scanning mirror. The exit facet of the semiconductor laser (ls) lies in the entrance focus. The semiconductor laser is also capable of illuminating an entrance pinhole in the entrance focus. The optical imaging system conducts the light that is reflected from the focal plane as a return beam, via the polarising beam splitter (pbs), to an avalanche photodiode (apd). Furthermore, the microscope objective (mo) is preceded by a ¼λ-plate so that the polarisation of the return beam is perpendicular to the polarisation of the monitoring beam. The polarising beam splitter (pbs) thus separates the return beam from the monitoring beam. An optical display unit utilizes the output signal of the avalanche photodiode to form the image (img) of the focal plane in or on the object to be examined, the image being displayed on a monitor. In practice, the optical display unit is a workstation and the image is realized by deriving an electronic video signal from the output signal of the avalanche photodiode by means of the processor of the workstation. This image is used to monitor the spectroscopic examination, notably to excite the target region such that the excitation area falls onto the target region and receiving scattered radiation from the target region. The Raman spectroscopy device (exs) includes an excitation system (exs) which is in this case constructed as an Ar-ion/Ti-sapphire laser which produces the excitation beam in the form of an 850 nm infrared beam (exb). The Ti-sapphire laser is optically pumped with the Ar-ion laser. Light of the Ar-ion laser is suppressed by means of an optical filter (of). A system of mirrors conducts the excitation beam to the optical coupling unit (oc) and the optical coupling unit conducts the excitation beam along the monitoring beam (irb) after which the microscope objective focuses it in the focal plane at the area of the focus of the monitoring beam. The optical coupling unit (oc) forms the beam combination unit. The optical coupling unit conducts the excitation beam along the optical main axis of the microscope objective, that is, along the same optical path as the monitoring beam. The Raman scatter is reflected to the entrance of a fiber (fbr) by the optical coupling unit (oc). The Raman scattered infrared light is focussed on the fiber entrance in the detection pinhole by the microscope objective (mo) and a lens (13) in front of the fiber entrance (fbr-i). The fiber entrance itself acts as a detection pinhole. The optical imaging system establishes the confocal relationship between the entrance focus, where the semiconductor laser (ls) is present, the exit focus at the area of the detail of the object (obj) to be examined and the detection focus in the fiber entrance (fbr-i). The fiber (fbr) is connected to the input of a spectrometer (spin) with a CCD detector (COD). The spectrometer with the COD detector are incorporated into the detector system (dsy) which records the Raman spectrum for wavelengths that are smaller than approximately 1050 nm. The output signal of the spectrometer with the CCD detector represents the Raman spectrum of the Raman scattered infrared light. In practice, this Raman spectrum occurs in the wavelength range beyond 730 nm or beyond 860 nm, depending on the excitation wavelength. The signal output of the COD detector is connected to a spectrum display unit (spd), for example a workstation which displays the recorded Raman spectrum (spct) on a monitor.

In practice the functions of the optical display unit and the spectrum display unit can be carried out by means of the same workstation. For example, separate parts (windows) of the display screen of the monitor are used for simultaneous display of the optical image and the Raman spectrum.

Figure 2:
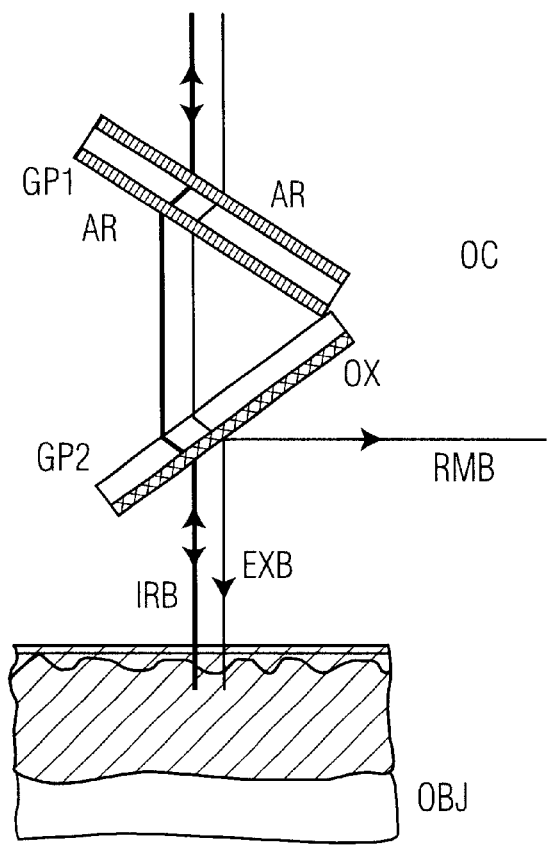
FIG. 2 is a more detailed diagrammatic representation of the beam combination unit in the form of an optical coupling system used in the analysis system in accordance with the invention.

FIG. 2 is a more detailed diagrammatic representation of the optical coupling system used in the analysis system in accordance with the invention. The optical coupling unit (oc) includes a partial reflection plate (gp2) and a correction plate (gp1) These partial reflection and correction plates are, for example, glass plates of a thickness of 1.5 mm which are arranged transversely of (preferably perpendicularly to) the plane of the monitoring beam and the excitation beam and also perpendicularly to one another. At the side of the microscope objective, the glass plate (gp2) is provided with an optical filter coating in the form of an oxide surface coating (ox) which has a reflectivity of 0.80 for the wavelength ranges 720–740 nm and 860–1050 nm. This glass plate (gp2) acts as the optically selective filter in the form of a beam splitter which separates the Raman scattered light from the monitoring beam. The glass plate (gp2) transmits the infrared light of the monitoring beam practically without attenuation, but the monitoring beam is shifted slightly due to refraction. The correction plate (gp1) shifts the monitoring beam back again, so that the return monitoring beam is accurately focussed onto the avalanche photodiode (apd).

The excitation beam that is partly reflected from the object (obj) can also be transmitted to some extent by the optical coupling unit (oc) and the reflected excitation beam can be used to indicate the spot (spt) in the optical image (img) where the excitation beam is incident on the object.

An anti-reflection layer (ar) is provided on both sides of the correction plate. The anti-reflection layers have a reflectivity of less than 0.015 for 834 nm, so that the monitoring beam is hardly reflected.

Very good results are obtained with a filter coating having transmission and reflection properties (for both polarisation directions) as listed in Table 1. Table 1 lists suitable transmission and reflection coeffcients for the various wavelength ranges at issue.

TABLE 1 optical filter coating

|  | excitation | monitoring | multi photon fluorescence | Raman scattering |
|---|---|---|---|---|
| $\lambda$ (nm) | 720–740 | 850 | 834 | 400–600 | 730–1050 860–1050 |
| R | ≧0.8 | 0.9 | <0.2 | ≧0.95 | ≧0.8 ≧0.9 ≧0.95 |
| T | <0.2 | 0.1 | ≧0.8 |  |  |

Such an optical filtercoating excellently reflects the exciation beam towards the target region. The monitoring beam is hardly attenuated and the scattered readiation is efficiently coupled out to the detector system.

Table 2 shows suitable reflectivities of the anti-reflex coatings for two wavelengths

TABLE 2 anti-reflex coating

| $\lambda$ (nm) | 834 | 850 |
|---|---|---|
| R | <0.015 | 0.85 |

Figure 3:
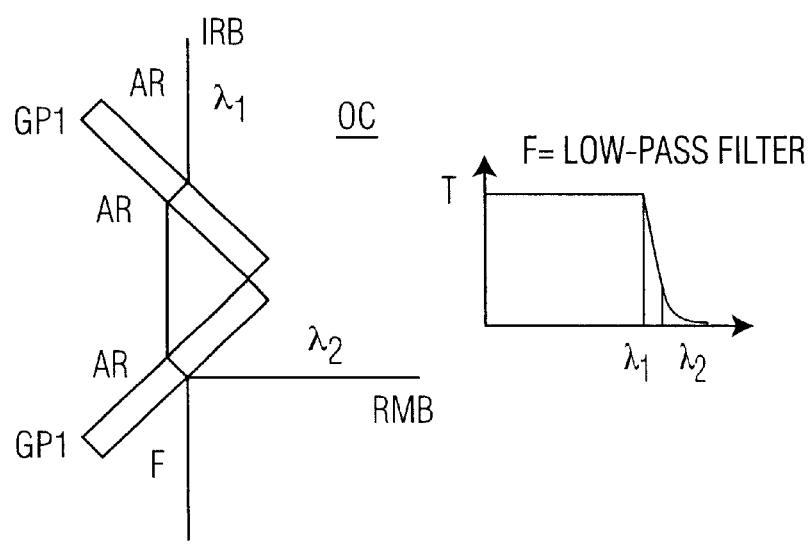
FIGS. 3 and 4 show diagrammatic representations of alternatives of the optical coupling system represented in terms of optical filters.
Figure 4:
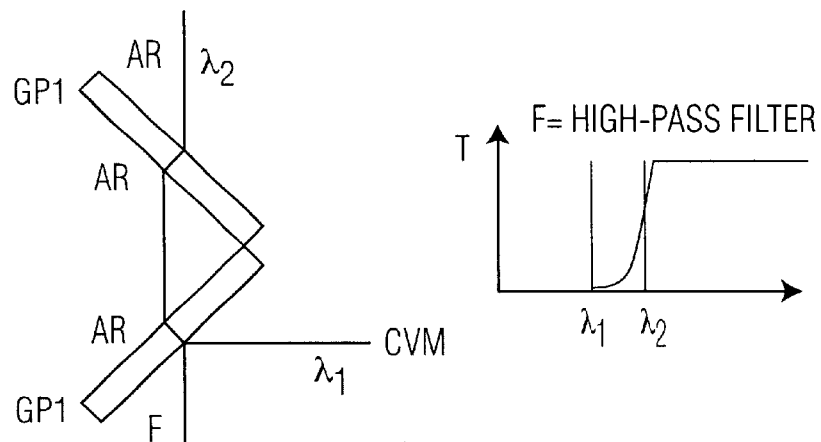

FIGS. 3 and 4 show diagrammatic representations of alternatives of the optical coupling system represented in terms of optical filters. The optical filter comprises the two plates gp1 and gp2 wherein gp1 is a beam position shift correction, and plate gp2 is a low pass filter F. The other plate side of gp2 and both sides of plate gp1 are, preferably, Anti-Reflection coated (AR). As to the incident beams:

the monitoring beam (irb) is transmitted through the two filter plates (1, 2) with T>90% for both p and s polarisation orientations. The Raman excitation beam (exb) is reflected at plate gp2, e.g. with R~85%. As to the returning beams: most of the elastically scattered Raman excitation beam is reflected by F towards the Raman spectrograph and detector, a small part of this beam is transmitted towards the confocal video microscope of the monitoring system, to provide a visible spot in the image. The inelastically scattered Raman light ($\lambda_r > \lambda_2$) is reflected at F (preferably R=100%) towards the detection system. Plates gp1 and gp2 can be interchanged with entrée position of Raman excitation beam at plate gp1, as shown in FIG. 4. The filter can be arranged such that the entrance of the confocal video microscope and Raman excitation beam is interchanged and the filter F is now a high pass filter (gp1 is a beam position shift correction, and plate gp2 is a high pass filter F). The other plate side of gp2 and both sides of plate gp1 can be Anti-Reflection coated (AR).

In both schemes the beam shift correction plate could be removed, however, then the objective lens has to be shifted with respect to the optical axis.

Figure 5:
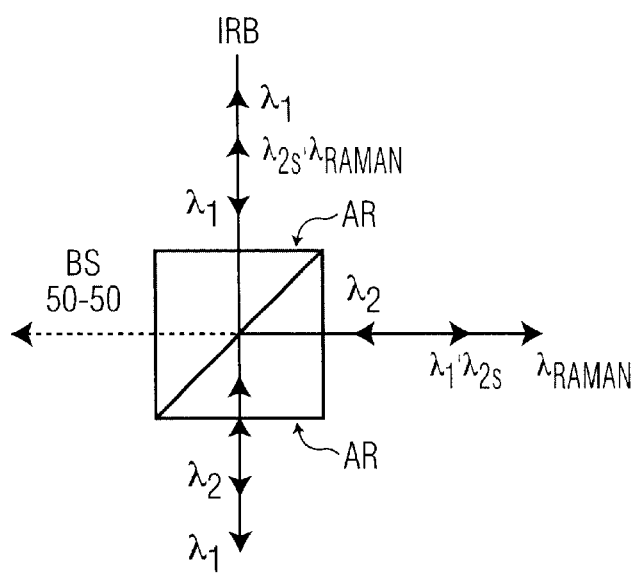
FIG. 5 shows a simple embodiment of the beam combination unit.

FIG. 5 diagrammatically shows a simple embodiment of the beam combination unit in the form of a set of beam-splitting prisms. Of the monitoring beam ($\lambda_1$), the Raman excitation beam ($\lambda_2$), the elastically scattered Raman beam ($\lambda_{2s}$), and inelastically scattered Raman light ($\lambda_{Raman}$) about 50% is transmitted by beamsplitter BS; 50% is reflected. This way, about 50% of collected $\lambda_{2s}$ and $\lambda_{Raman}$ reaches the confocal video microscope (lso), providing a visible spot in the image. Anti-reflection coatings AR are optional.

Figure 6:
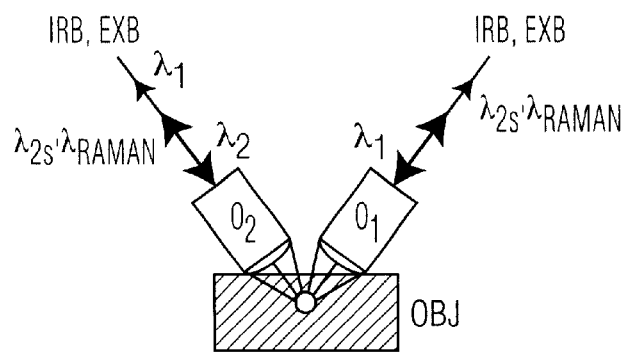
FIG. 6 shows an even more simple embodiment of the beam combination unit.

FIG. 6 shows an even more simple embodiment of the beam combination unit. In this very simple alternative two identical objectives can be used($O_1$ and $O_2$, respectively). The monitoring beam $\lambda_1$ and Raman excitation beam $\lambda_2$ are focussed onto the same spot in the skin. Part of the Raman excitation beam $\lambda_2$ is scattered elastically, collected by $O_1$, and detected by the confocal video microscope, providing a visible spot in the image. The objectives should move simultaneously during depth scan.

Figure 7:
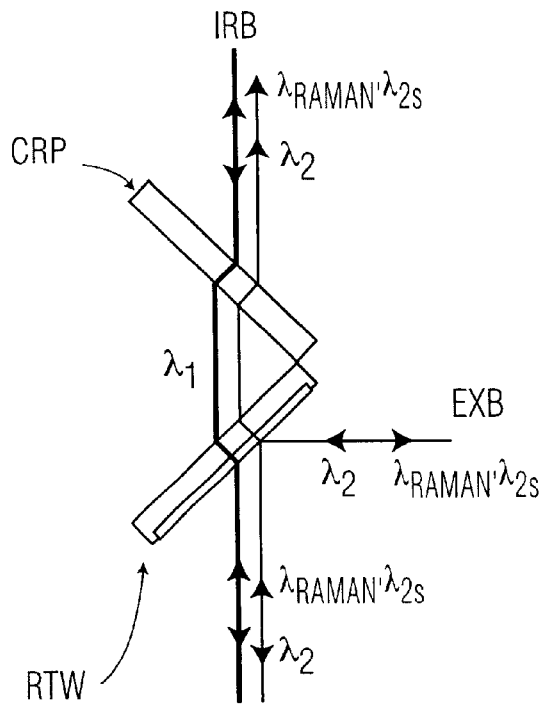
FIGS. 7 and 8 show a diagrammatic representation of a further beam combination unit for the analysis apparatus according to the invention.
Figure 8:
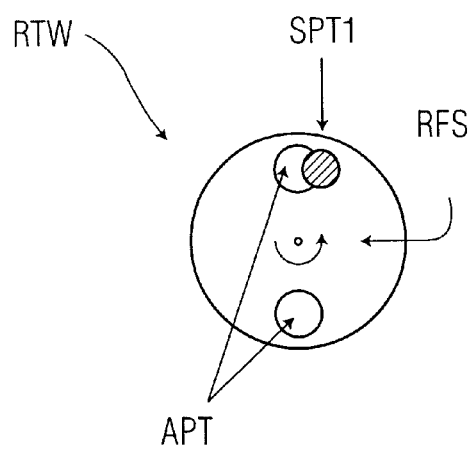

FIGS. 7 and 8 show a diagrammatic representation of a further beam combination unit for the analysis apparatus according to the invention. The beam combination unit shown in FIGS. 7 and 8 operate on the basis of temporal aperture sharing. The monitoring beam ($\lambda_1$) and Raman excitation ($\lambda_2$) beam are combined at the reflection/transmission unit (R/t-u) in the form of a rotating wheel (rtw) coated with a reflecting pattern. FIG. 7 shows a side elevation of the rotating wheel (rtw). FIG. 8 shows a front view of the rotating wheel. During periods of the rotation, the beams hit a reflecting layer (rfs) that forms the reflecting section. In these periods the target area is not imaged, while the excitation beam $\lambda_2$ is reflected onto the sample, and the elastically scattered Raman excitation beam ($l_{2s}$) and in-elastically scattered Raman light ($\lambda_{Raman}$) are reflected back to the Raman spectrometer (spm). During other periods of the rotation, $\lambda_1$ and $\lambda_2$ are transmitted through transmissive openings in the reflecting coating, such as simple holes (apt), forming the transmissive section and no Raman signal is generated. The monitoring beam $\lambda_1$ is transmitted onto the sample, transmitted again on the way back, and part of the image is being built. At certain moments during the rotation, parts of both $\lambda_1$ and $\lambda_2$ beams are transmitted through the hole, (shown as the spot spt1) and parts are reflected by the coating. Also during those moments, parts of $\lambda_{2s}$ and $\lambda_{Raman}$ are transmitted through the hole, and produce a visible spot in the image.

Figure 9A:
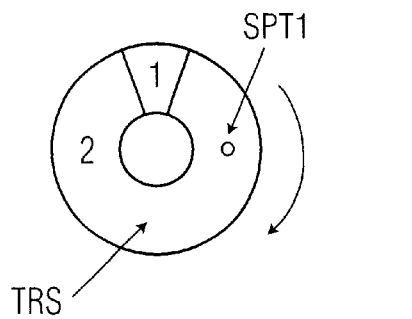
FIGS. 9a and 9b show further examples of reflector/transmission units that may be employed in the beam combination unit.
Figure 9B:
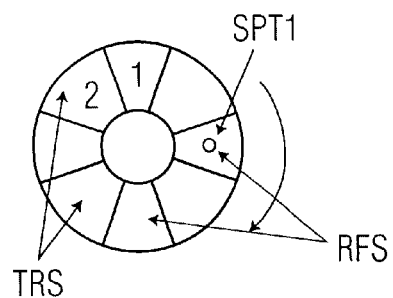

FIGS. 9a and 9b show further examples of reflector/transmission units that may be employed in the beam combination unit. These reflector/transmission units operate on the principle of operation similar to "temporal aperture sharing":

The monitoring beam ($\lambda_1$) and Raman excitation ($\lambda_2$) beam are combined at a rotating wheel coated with a pattern of higher and lower reflective material. The higher reflective parts in this pattern form the reflective sections and the lower reflective parts form the tranmsissive sections. During periods of the rotation, the beams hit the higher reflective parts of the pattern. The excitation beam $\lambda_2$ is for the larger part (e.g. 90%) reflected onto the sample, and the elastically scattered Raman excitation beam ($\lambda_{2s}$) and inelastically scattered Raman light ($l_{Raman}$) are mainly (e.g. 90%) reflected back to the Raman spectrometer (spm). A small portion (e.g. 10%) of the scattered radiation $\lambda_{2s}$ and $\lambda_{Raman}$ are transmitted and reach the confocal video microscope, producing a visible spot in the image. During other periods of the rotation, $\lambda_1$ and $\lambda_2$ are mainly transmitted and a low Raman signal; the reflected monitoring beam $\lambda_1$ is transmitted onto the sample, transmitted again on the way back, and contributes to the image. Optional AR coatings are employed on both sides of correction plate or on the back of wheel. In the examples of FIGS. 9a and 9b variable are: the pattern higher-lower reflectivity, the ratio $R_1/R_2$ and the frequency of rotation.

Figure 10:
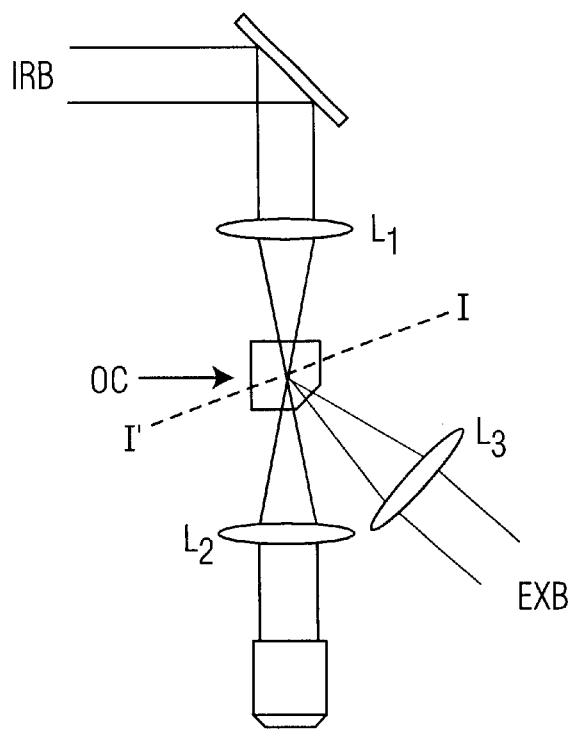
FIG. 10 shows another simple example of the beam combination unit.
Figure 11:
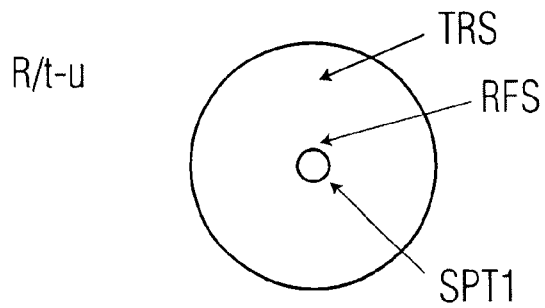
FIG. 11 shows a cross sectional view of the reflector/transmission unit incorporated in the beam combination unit of FIG. 10.

FIG. 10 shows another simple example of the beam combination unit and FIG. 11 shows a cross section along the line I–I' of the reflector/transmission unit incorporated in the beam combination unit of FIG. 10. The Raman excitation beam and the monitoring beams are combined at a spot reflector: the Raman excitation beam ($\lambda_2$) is focussed onto a small reflecting dot forming the reflective section (rfs), reflected, and reaches the sample. On the way back, the elastically scattered Raman excitation beam ($\lambda_2$) and Raman light ($\lambda_{Raman}$) are reflected by the same dot, and reach the Raman spectrograph. The monitoring beam ($\lambda_1$) is focussed by lens $L_1$. Lenses L1, L2 and L3 are identical, and positioned such, that the centres of their focal planes coincide. During scanning, the monitoring beam ($\lambda_1$) is transmitted through the transmissive section (trs) of the reflection-transmission-unit most of the time, and a image is being built. When the monitoring beam hits the reflecting dot, a dark spot appears in the image, indicating the position of the Raman spot in the sample. If the reflectivity of the dot is less than 100% (e.g. 90%), a corresponding fraction of $\lambda_{2s}$ and $\lambda_{Raman}$ reaches the confocal video microscope, producing a lighter spot on top of (or within) the darker spot in the image, then by switching $\lambda_2$ on and off (e.g. by means of a shutter), the alignment with $\lambda_1$ can be checked. Optionally AR coatings at the surfaces of the beam combining element spot reflector and lenses L may be combined into one element. The example shown in FIGS. 10 and 11 provide a very simple beam combination unit.

Figure 12:
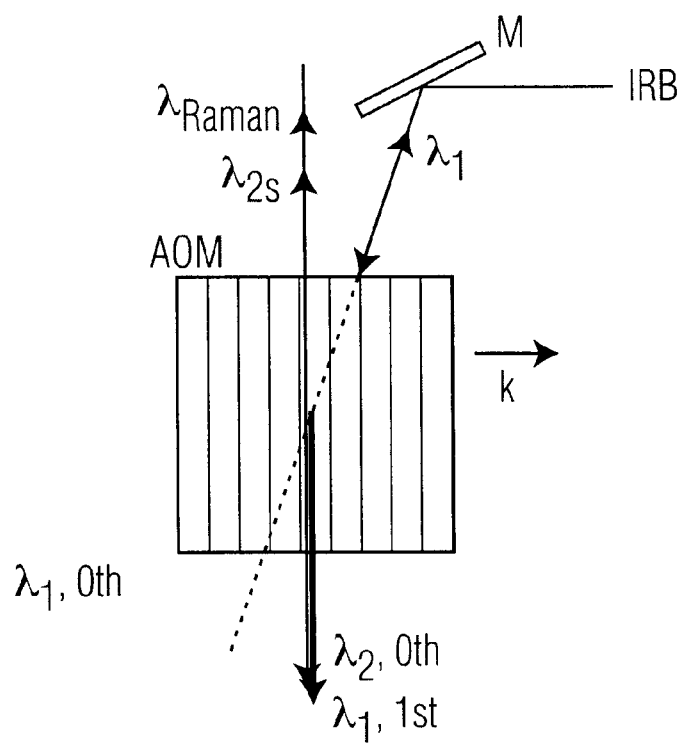
FIG. 12 shows another example of the beam combination unit including an acousto-optic modulator, FIG. 13 diagrammatically shows an embodiment of the analysis apparatus according to the invention including an optical separation system, FIG. 14 diagrammatically shows a further embodiment of the analysis apparatus according to the invention wherein the monitoring system is an orthogonal polarised spectral imaging arrangement, FIG. 15 diagrammatically shows a further embodiment of the analysis apparatus according to the invention wherein the excitation beam scans the target area substantially transverse to its longitudinal axis

FIG. 12 shows another example of the beam combination unit including an acousto-optic modulator. The monitoring beam ($\lambda_1$) and Raman excitation beam $\lambda_2$) are combined by means of an acousto-optic modulator. The 0th order diffracted $\lambda_2$ beam arrives at the sample, producing elastically and inelastically (Raman) scattered light ($\lambda_{2s}$ and $\lambda_{Raman}$ respectively). The 0th order diffracted $\lambda_{2s}$ and $\lambda_{Raman}$ beams reach the Raman detector. A small fraction of the $\lambda_{2s}$ and $\lambda_{Raman}$ beams is diffracted into the direction of the confocal video microscope providing a visible spot in the image. The frequency of the acoustic wave travelling through the AOM is chosen such, that the 1st order diffracted $\lambda_1$ beam (of slightly different wavelength, $\lambda_1'$) can be made parallel to the 0th order diffracted $\lambda_2$ beam. Coming back from the sample, the −1 order diffracted $\lambda_1'$ beam (again of wavelength $\lambda_1$) travels along the same path as the original $\lambda_1$ beam, and reaches the confocal video microscope.

Figure 13:
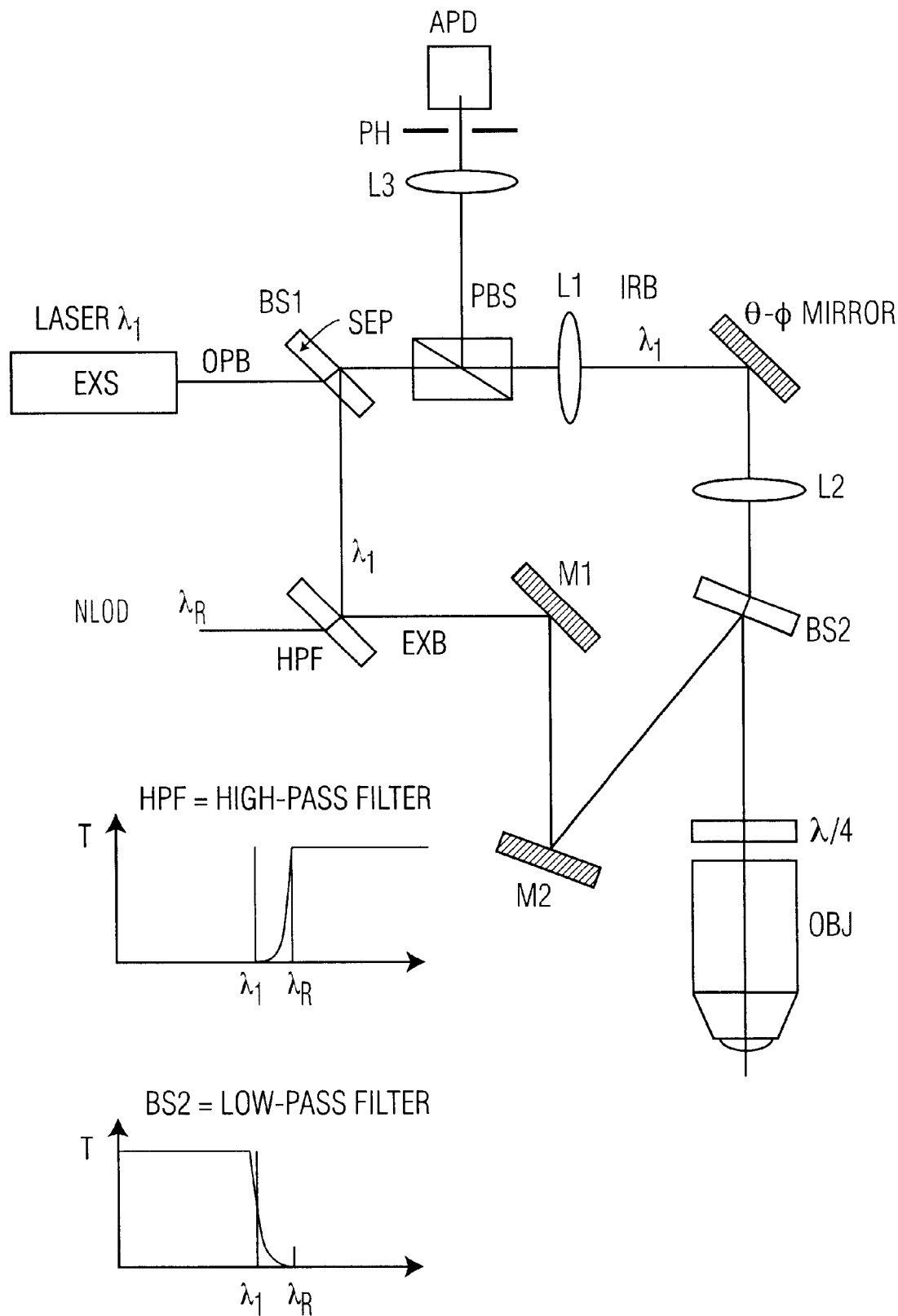

FIG. 13 diagrammatically shows an embodiment of the analysis apparatus according to the invention including an optical separation system. A laser at ($\lambda_1$) forms the radiation source that is used for confocal imaging and simultaneously for Raman excitation. The beam is split in two by the optical separation system (sep) formed by an (e.g. 20–80%) beam splitter (BS1). Part is used for confocal imaging, the other part is used for Raman excitation. The monitoring beam is linearly polarised by the polarising beam splitter (PBS). The scanning beam path in the confocal video microscope is deflected in x-y plane by the θ-φ mirror to form the image. Lenses L1 and L2 are used for beam expansion and L2 is used to image the central part of the θ-φ mirror on to the entrance pupil of the microscope objective (mo). In this way laser light reflected of the θ-φ mirror always enters the objective at the same position, irrespective of the actual θ-φ position of the θ-φ mirror. The linearly polarised monitoring ($\lambda_1$) beam is transformed to circularly polarised light by the quarter wave plate (¼λ). The Raman excitation beam is reflected at the high pass filter HPF and directed towards the objective via the mirrors M1 and M2, and reflecting beam-splitter (BS2). On the return path reflected light from the object is transformed to linearly polarised light again however, shifted by 90° orientation, with respect to the polarisation orientation of the incoming beam. The transmitted light (partly the monitoring beam and partly the elastically scattered Raman light) trough the reflecting beam splitter BS2 is then deflected by the polarising beam splitter PBS towards the APD detector to form the image and the Raman spot in the image. Elastically and inelastically scattered Raman light from the object is reflected at the BS2. The inelastically scattered Raman light ($\lambda_R$) is transmitted through the high pass filter HPF and directed towards the Raman detection path. The beamsplitter BS2 can be exchanged by the spot reflector as shown in FIGS. 7 and 8.

Figure 14:
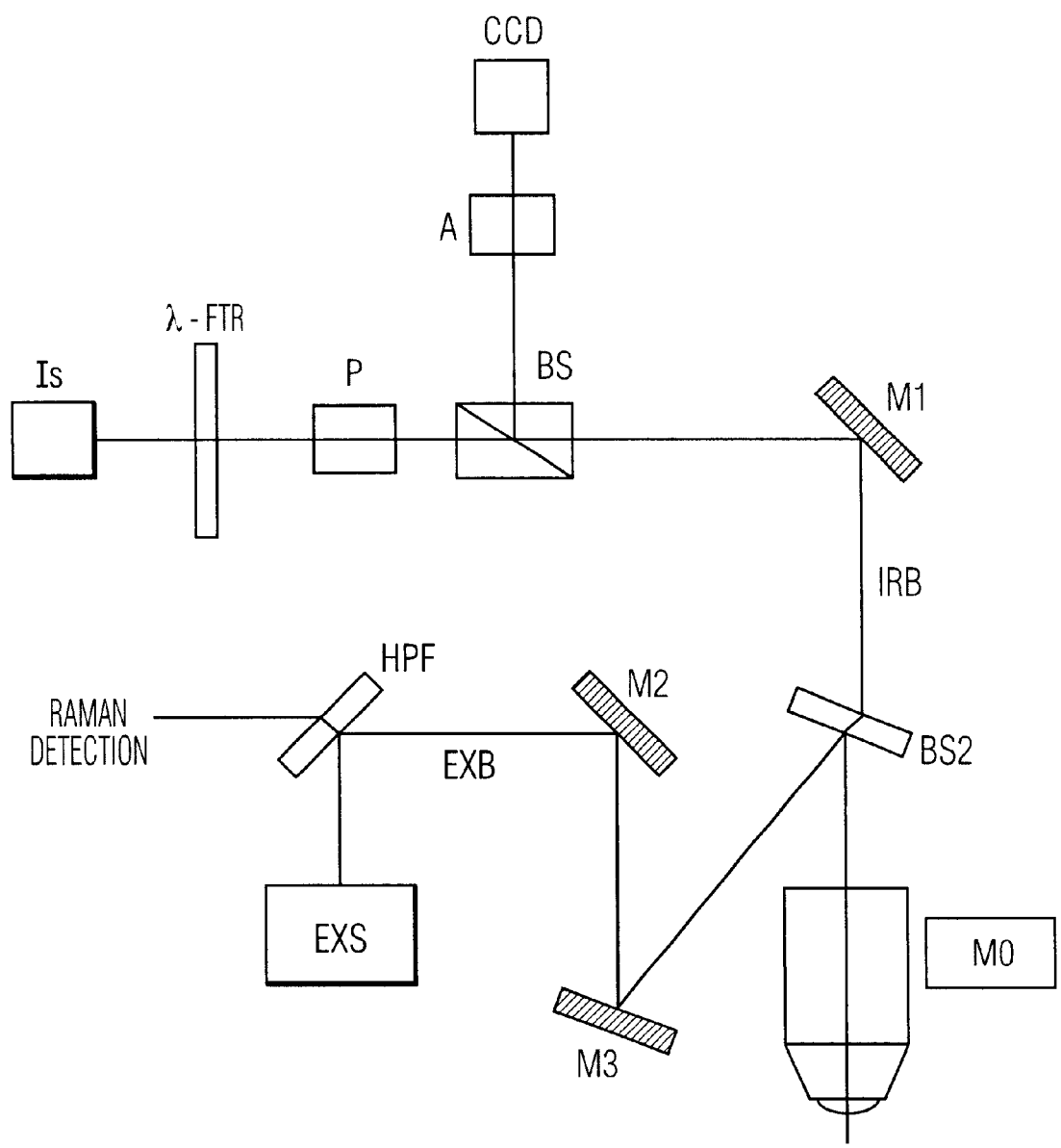

FIG. 14 diagrammatically shows a further embodiment of the analysis apparatus according to the invention wherein the monitoring system is an orthogonal polarised spectral imaging arrangement. This embodiment combines imaging by OPSI and Raman spectroscopy. For orthogonal polarised spectral imaging (OPSI) a light source is used at a specific wavelength band. To achieve this a white light source is filtered by a band pass filter (λ-Ftr). The light is linearly polarised by the polariser (P). The light is then focused in the object by the objective lens (Obj). The reflected light is detected through an analyser at orthogonal polarisation orientation. This means that only depolarised light is detected which originates from multiply (diffusely) scattered light deep in the turbid object (tissue). The back scattering of these photons produces a sort of 'backlight illumination' which gives a more or less homogenous brightness in the image at the CCD detector (CCD see FIG. 1). By proper selection of the wavelength (λ-Ftr) corresponding to (partly) absorption in shallow objects (such as capillaries in skin) these objects in contrast appear dark (through absorption) on a bright background. A Raman excitation beam can be coupled in the OPSI image in a similar fashion as in confocal imaging using a filter or other beam combination unit. The advantage of OPSI is especially its compactness and low cost.

Figure 15:
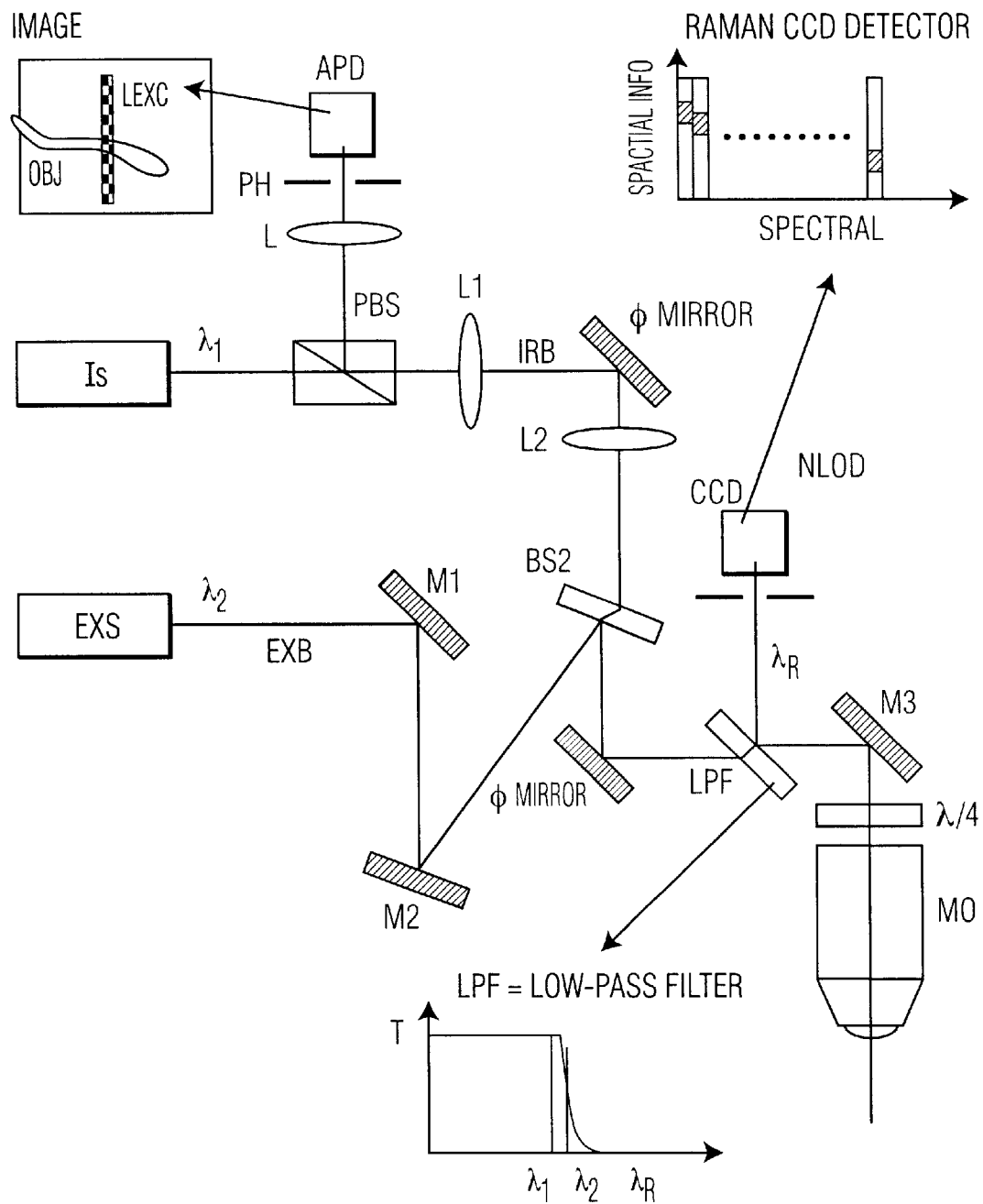

FIG. 15 diagrammatically shows a further embodiment of the analysis apparatus according to the invention wherein the excitation beam scans the target area substantially transverse to its longitudinal axis. The scanning monitoring beam path in the confocal video microscope is deflected in x-y plane by the separate θ and φ mirrors to form the image. The Raman excitation beam is now deflected from the φ mirror to produce a line in the image. This elongate excitation area is displayed in the image (lexc) and extends transverse to the target region in the object, e.g. a capillary blood vessel. This has the advantage to be less sensitive to movements of objects in the region of interest in the image. Via a low pass filter LPF the reflected monitoring beam and part of the Raman excitation beam are transmitted to form the images on the detector. The inelastically scattered Raman light is reflected of the LPF filter and detected via slit to form a line on the CCD detector containing spatial information along one dimension and spectral information along the other dimension.

Figure 16:
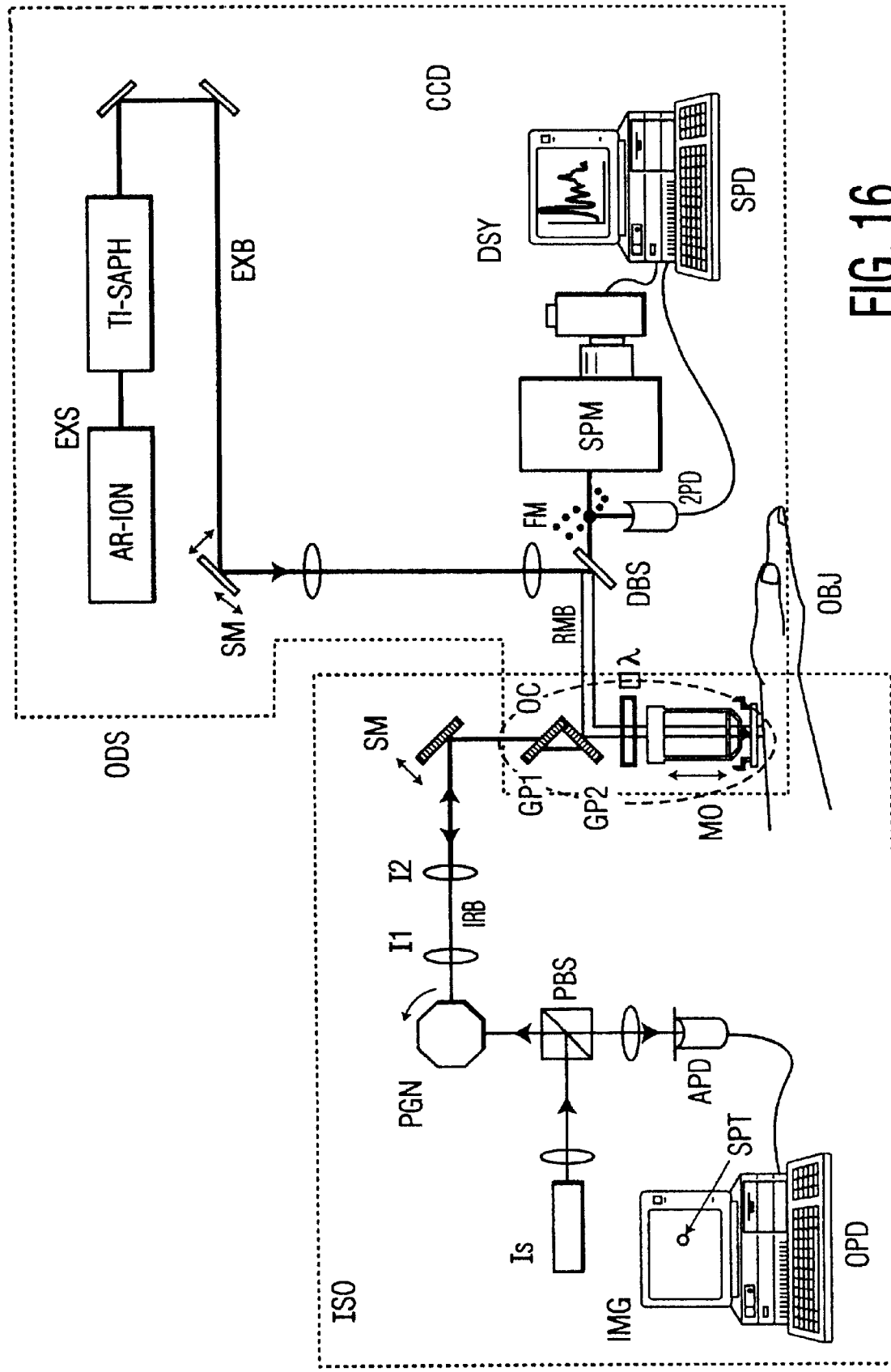
FIG. 16 is a diagrammatic representation of a second embodiment of the analysis system in accordance with the invention.

FIG. 16 is a diagrammatic representation of a second embodiment of the analysis system in accordance with the invention. The embodiment shown in FIG. 16 utilises a multi-photon or non-linear optical detection system in the form of a multi-photon fluorescence device. A dichroic beam splitter (dbs) transmits the multi-photon fluorescence light that is generated by the excitation beam in the object to be examined. Such a dichroic beam splitter separates light of different wavelengths, so of different colours. The analysis system also includes a folding mirror (fm) that is arranged behind the birefringent beam splitter. In the position that is shown in FIG. 16 the multi-photon light fluorescence light is conducted to a photodetector (2pd). The photodetector is connected to the workstation (spd). The processor of the workstation (spd) derives an electronic video signal from the output signal of the photodetector. When use is made of a CCD detector, the output signal itself can be used as the electronic video signal. This electronic video signal represents the multi-photon fluorescence image that is displayed on the monitor. The folding mirror can also be removed from the light path, so that the multi-photon fluorescence light is transmitted to the spectrometer (spm) in order to record the multi-photon fluorescence spectrum.

What is claimed is:

1. An analysis apparatus including a spectroscopic analysis apparatus comprising:

a monitoring system for emitting a monitoring beam to image a target region during a monitoring period;

an excitation system for emitting an excitation beam to excite at least a portion of the target region during an excitation period overlapping with the monitoring period, the excited portion of the target region constituting an excitation area which is thus imaged by the monitoring beam; and an image display arranged to simultaneously display the imaged target region and the imaged excitation area.

2. An analysis apparatus as claimed in claim 1 further including a beam combination unit to direct the excitation beam and the monitoring beam to the target region and separate a reflected or transmitted monitoring beam and at least part of a reflected or transmitted excitation beam reflected from or passed through the target region from scattered radiation from the target region generated by the excitation beam.

3. An analysis apparatus as claimed in claim 2, wherein the beam combination unit reflects at least partially the scattered radiation and transmits at least partially, the reflected monitoring beam and the reflected excitation beam.

4. An analysis apparatus as claimed in claim 3, wherein one of the partial transmission and partial reflection of the beam combination unit are achieved in that the beam combination unit is alternatingly partial transmissive and partial reflective.

5. An analysis apparatus as claimed in claim 2, wherein the beam combination unit transmits at least partially the scattered radiation and reflects at least partially, the reflected monitoring beam and the reflected excitation beam.

6. An analysis apparatus as claimed in claim 2, wherein the beam combination unit comprises a reflector/transmission unit having a reflective section at least partially reflective for the excitation beam and substantially opaque for the monitoring beam and a transmissive section at least partially transmissive for the monitoring beam and the reflected monitoring beam.

7. An analysis apparatus as claimed in claim 6, wherein the reflector/transmission unit is movable or rotatable relative to the excitation system and the monitoring system so as to alternatingly place the reflective section in the excitation beam and the transmissive section in the monitoring beam and vice versa.

8. An analysis apparatus as claimed in claim 2, wherein the beam combination unit comprises a reflector/transmission unit having a transmissive section substantially transmissive for the excitation beam and the scattered radiation and a reflective section substantially reflective for the monitoring beam.

9. An analysis apparatus as claimed in claim 1, further comprising a radiation source to emit an output beam and an optical separation system to separate the monitoring beam and the excitation beam from the output beam.

10. An analysis apparatus as claimed in claim 2, wherein the beam combination unit includes an acousto-optic modulator.

11. An analysis apparatus as claimed in claim 2, wherein the beam combination unit is arranged to move the excitation beam in the target region.

12. An analysis apparatus as claimed in claim 1, further comprising a detection system for detecting scattered radiation from the target region generated by the excitation beam, wherein the monitoring system includes a confocal video microscope and the detection system having a confocal relationship with the confocal video microscope.

13. An analysis apparatus as claimed in claim 1, wherein the monitoring system is selected from the group consisting of an orthogonal polarised spectral imaging arrangement, an optical coherence tomography arrangement, an optical Doppler tomography arrangement, a photo-acoustic imaging arrangement and a multiphoton microscopy arrangement.

14. An analysis apparatus as claimed in claim 1, wherein the excitation system is arranged to scan the excitation beam substantially transverse to a longitudinal axis of the target area.

15. An analysis apparatus as claimed in claim 1, wherein the target region is defined in or on an object to be examined, the monitoring system comprising means for moving the monitoring beam relative to the object being examined.

16. An analysis apparatus as claimed in claim 1, further comprising a spectrum display unit for displaying data obtained from the excitation of the target region by the excitation beam, the image display and the spectrum display unit being a common monitor such that the image of the target region is displayed on a portion of a screen of the monitor simultaneously with the data obtained from the excitation of the target region which is displayed on another portion of the screen of the monitor.

17. A method for analyzing a composition of an object to be examined, comprising the steps of:

emitting a monitoring beam to image a target region in or on the object during a monitoring period;

emitting an excitation beam to excite at least a portion of the target region during an excitation period overlapping with the monitoring period, the excited portion of the target region constituting an excitation area which is thus imaged by the monitoring beam; and simultaneously displaying the imaged target region and the imaged excitation area.

18. A method for spectral non-invasive analysis of a composition of blood comprising the steps of:

imaging a target region by emitting a monitoring beam substantially coinciding with a blood vessel during a monitoring period;

exciting at least a portion of the target region with an excitation beam during an excitation period substantially overlapping with the monitoring period, the excited portion of the target region constituting an excitation area which is thus imaged by the monitoring beam;

simultaneously displaying the imaged target region and the imaged excitation area; and detecting scattered radiation from the target region generated by the excitation beam with imaging the target region using the monitoring beam.

19. The method as claimed in claim 18, wherein the monitoring beam is emitted confocally.

20. The method as claimed in claim 18, wherein the step of detecting scattered radiation from the target region comprises the step of detecting scattered radiation from the target region generated by the excitation beam confocally with imaging the target region using the monitoring beam.

* * * * *